(12) United States Patent
Falter et al.

(10) Patent No.: US 8,991,258 B2
(45) Date of Patent: Mar. 31, 2015

(54) LINEAR SCANNER WITH ROTATING COUPLING FLUID

(75) Inventors: Stephan Falter, Simmerath (DE); Kurt Guenter Fuchs, Ruppichteroth (DE); Dieter Lingenberg, Hurth (DE); Cord Heinrich Asche, Hurth (DE)

(73) Assignee: General Electric Company, Schenectady, NY (US)

( * ) Notice: Subject to any disclaimer, the term of this patent is extended or adjusted under 35 U.S.C. 154(b) by 404 days.

(21) Appl. No.: 13/468,059

(22) Filed: May 10, 2012

(65) Prior Publication Data

US 2013/0298685 A1  Nov. 14, 2013

(51) Int. Cl.
| | | |
|---|---|---|
| G01N 29/00 | (2006.01) | |
| G01N 29/04 | (2006.01) | |
| G01N 29/27 | (2006.01) | |
| G01N 29/28 | (2006.01) | |
| G01N 29/22 | (2006.01) | |

(52) U.S. Cl.
CPC ............... *G01N 29/04* (2013.01); *G01N 29/27* (2013.01); *G01N 29/28* (2013.01); *G01N 29/223* (2013.01); *G01N 2291/262* (2013.01); *G01N 2291/2634* (2013.01)
USPC .................................. 73/644; 73/628; 73/635

(58) Field of Classification Search
CPC .................. G01N 29/04; G01N 29/23; G01N 2291/2634; G01N 29/27; G01N 29/28; G01N 2291/262
USPC ..................................... 73/644, 622, 628, 635
See application file for complete search history.

(56) References Cited

U.S. PATENT DOCUMENTS

| 4,404,853 A | * | 9/1983 | Livingston | ....................... 73/622 |
|---|---|---|---|---|
| 4,641,531 A | * | 2/1987 | Reeves et al. | .................... 73/622 |
| 5,303,592 A | | 4/1994 | Livingston | |
| 5,473,943 A | | 12/1995 | Schoenen et al. | |

(Continued)

FOREIGN PATENT DOCUMENTS

| FR | 2796153 A1 | 1/2001 |
|---|---|---|
| GB | 1086286 A | 10/1967 |

(Continued)

OTHER PUBLICATIONS

Search Report from GB Application No. 1308405.8 dated Sep. 18, 2013.

*Primary Examiner* — J M Saint Surin
(74) *Attorney, Agent, or Firm* — Cooper Legal Group, LLC

(57) ABSTRACT

An inspection arrangement and an associated method for inspecting an elongate object. The arrangement includes a housing providing an interior space. The housing has an entrance and exit that are aligned. The arrangement includes a plurality of ultrasonic sensor arrays disposed to direct ultrasonic sensory pluses. Each sensor array has a plurality of ultrasonic sensors with each ultrasonic sensor positioned to direct a respective ultrasonic sensory pulse in a respective direction. The arrangement includes a fluid delivery device that delivers a coupling fluid into the interior space. The coupling fluid transmits the ultrasonic sensory pluses to the elongate object. The arrangement includes a plurality of redirecting elements associated with the plurality of ultrasonic sensor arrays. Each redirecting element is positioned such that ultrasonic sensory pluses from the respective ultrasonic sensor array proceed through the respective redirecting element and are redirected along a different direction.

13 Claims, 5 Drawing Sheets

(56) References Cited

U.S. PATENT DOCUMENTS

| | | |
|---|---|---|
| 6,739,188 B1 | 5/2004 | Prause |
| 6,748,808 B2 * | 6/2004 | Lam et al. ............... 73/622 |
| 6,782,751 B2 * | 8/2004 | Linares et al. ........... 73/622 |
| 7,293,461 B1 * | 11/2007 | Girndt .................... 73/622 |
| 7,429,352 B2 * | 9/2008 | Bisiaux et al. ........... 266/99 |
| 2007/0074572 A1 | 4/2007 | Koch et al. |
| 2010/0212430 A1 | 8/2010 | Murai et al. |
| 2011/0120224 A1 | 5/2011 | Meinert et al. |
| 2011/0120225 A1 | 5/2011 | Meinert et al. |
| 2011/0132091 A1 | 6/2011 | Falter et al. |
| 2011/0138919 A1 | 6/2011 | Falter et al. |

FOREIGN PATENT DOCUMENTS

| | | |
|---|---|---|
| GB | 1470233 A | 4/1977 |
| GB | 2027199 A | 2/1980 |
| GB | 1572107 A | 7/1980 |
| GB | 2144852 A | 3/1985 |
| JP | H0639554 A | 2/1994 |

* cited by examiner

LINEAR SCANNER WITH ROTATING COUPLING FLUID

BACKGROUND OF THE INVENTION

1. Field of the Invention

The present invention relates to ultrasonic testing of elongate objects and specifically relates to ultrasonic testing of various elongate objects.

2. Discussion of the Prior Art

Testing of elongate objects, such as pipes and rods, is often necessary in order to determine whether the objects have defects, damage, flaws or the like and especially those located below a surface of the object. Moreover, because such elongate objects are often very long and/or very numerous, it is useful to conduct inspection of the objects in a continuous manner that can be accomplished during relative movement of each respective elongate object relative to an inspection arrangement.

Nondestructive ultrasonic testing of elongate objects is a known technique. Within one known example, an ultrasonic inspection arrangement permits inspection of sequential portions of an elongate object as the object moves relatively through surrounding ultrasonic sensor arrays of the ultrasonic inspection arrangement. Further within the known example, a fluid jacket environment is utilized to surround the respective portion of the elongate object with a coupling fluid (e.g., water) to couple the ultrasonic sensor arrays to the elongate object for efficient conduction of ultrasonic pulses. Such a type of inspecting arrangement can be referred to as a rotating water or "ROWA" inspecting arrangement. Sealing members at the leading and trailing edges of the fluid jacket environment bound the fluid jacket environment and yet permit passage of the elongate object due to the presence of circular apertures through the sealing members. As the elongate object is moved through the inspection arrangement and the fluid jacket environment thereof, the portions of the elongate object are sequential inspected via the ultrasonic sensor arrays. In general, such ultrasonic testing of the elongate objects with circular cross sections, such as hollow, circular cross-sectional pipes, has proven to be quite good and beneficial.

It should be appreciated that elongate objects of various circular diameters can be inspected via use of a single inspection arrangement. Some modification may be necessary to the inspection arrangement to accommodate the differing circular diameters. For example, the sealing members at the leading and trailing edges of the water jacket may need to be adjusted or interchanged to provide a different circular aperture size. It should be appreciated for larger diameter elongate objects, the aperture size of the seals should correspondingly be larger. As such, it is beneficial to have a sensing arrangement that can regularly accept variation of the elongate objects being processed for sensing.

It has been contemplated that there might be benefit to inspect other types (i.e., non-circular cross-section) elongate objects using a similar type of sensing arrangement. For example, some elongate objects are not circular in cross-section but contain one or more flat faces. Within a specific example, some elongate objects may have four flat surfaces and have a square cross sectional area. However, the sensor arrays within the known sensory arrangement are arranged/directed such that the sensor arrays are designed to best operate upon circular cross-sectional elongate objects. As such, the known sensory arrangement may not be able to provide optimal sensing of such non-circular cross-sectional elongate objects. As such, there is a need to provide a sensing arrangement that can readily provide inspection of both circular and non-circular cross sectional elongate objects.

BRIEF DESCRIPTION OF THE INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

In accordance with one aspect, the present invention provides an inspection arrangement for inspecting an elongate object. The arrangement includes a housing providing an interior space within which inspection is to occur. The housing has an entrance and an exit that are aligned on an axis for respective movement of the object relative to the interior space. The arrangement includes a plurality of ultrasonic sensor arrays disposed about the axis to direct ultrasonic sensory pluses within the housing. Each sensor array has a plurality of ultrasonic sensors with each ultrasonic sensor being positioned to direct a respective ultrasonic sensory pulse in a respective direction within the interior space. The arrangement includes a fluid delivery device for delivering a coupling fluid into the interior space. The coupling fluid engages the elongate object and transmits the ultrasonic sensory pluses to the elongate object. The arrangement includes a plurality of redirecting elements associated with the plurality of ultrasonic sensor arrays. Each redirecting element is positioned such that ultrasonic sensory pluses from the respective ultrasonic sensor arrays proceed through the respective redirecting element, and each redirecting element for redirecting at least some of the ultrasonic sensory pulses to proceed along a different direction.

In accordance with one aspect, the present invention provides a method of providing the inspection arrangement for inspecting an elongate object. The method includes providing a housing with an interior space within which inspection is to occur. The housing has an entrance and an exit that are aligned on an axis for respective movement of the object relative to the interior space. The method includes providing a plurality of ultrasonic sensor arrays disposed about the axis to direct ultrasonic sensory pluses within the housing. Each sensor array has the plurality of ultrasonic sensors with each ultrasonic sensor being positioned to direct a respective ultrasonic sensory pulse in a respective direction within the interior space. The method includes providing a fluid delivery device for delivering the coupling fluid into the interior space. The coupling fluid engages the elongate object and transmits the ultrasonic sensory pluses to the elongate object. The method includes providing a plurality of redirecting elements associated with the plurality of ultrasonic sensor arrays. Each redirecting element is positioned such that ultrasonic sensory pluses from the respective ultrasonic sensor array proceed through the respective redirecting element. Each redirecting element redirects at least some of the ultrasonic sensory pulses to proceed along a different direction.

BRIEF DESCRIPTION OF THE DRAWINGS

The foregoing and other aspects of the invention will become apparent to those skilled in the art to which the invention relates upon reading the following description with reference to the accompanying drawings, in which.

DETAILED DESCRIPTION OF THE INVENTION

Figure 1:
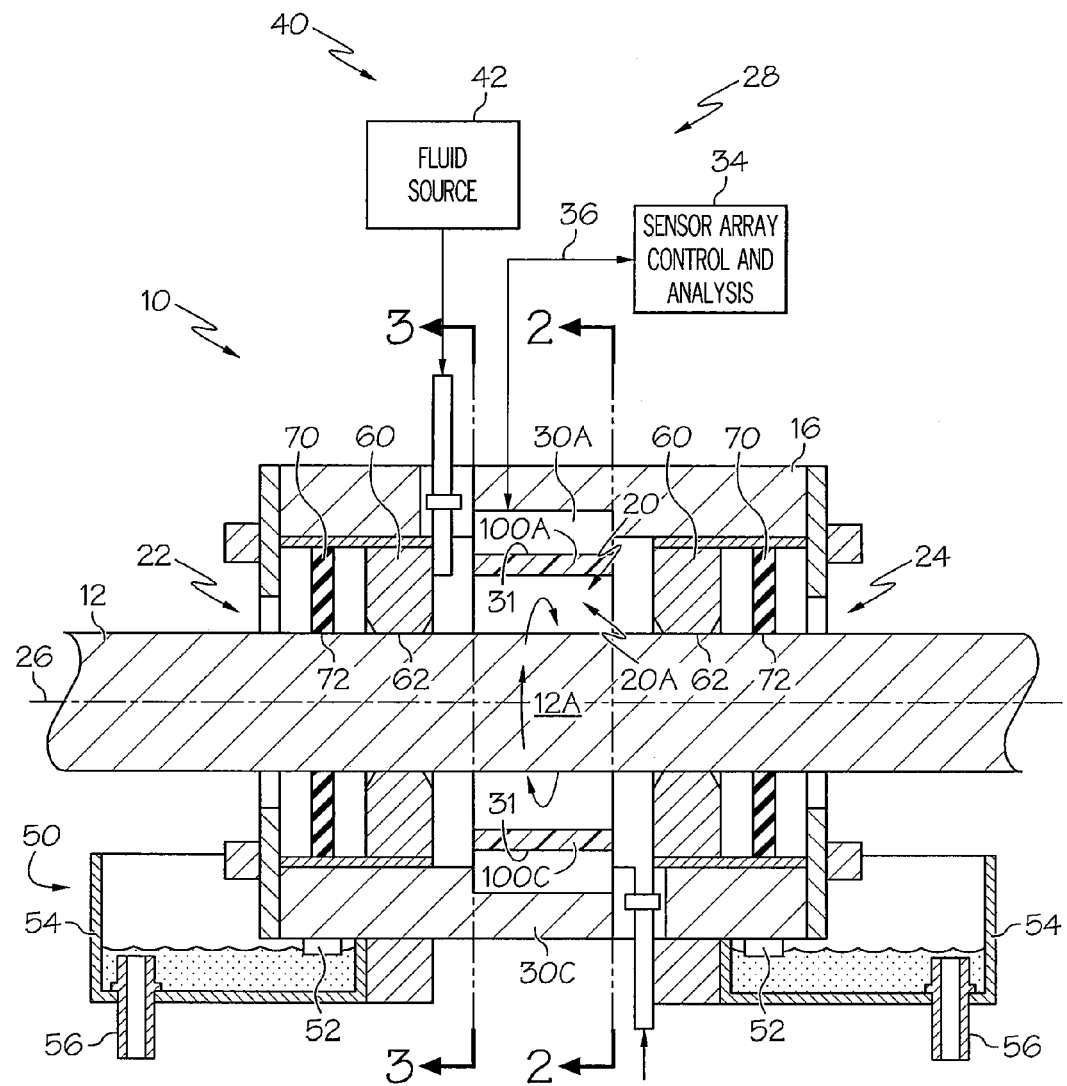
FIG. 1 is a schematized view of a section taken along an axis of an elongate object being ultrasonically inspected within an ultrasonic inspection arrangement in accordance with an aspect of the present invention.

Example embodiments that incorporate one or more aspects of the invention are described and illustrated in the drawings. These illustrated examples are not intended to be limitations upon the invention. For example, one or more aspects of the invention can be utilized in other embodiments and even other types of devices. Moreover, certain terminology is used herein for convenience only and is not to be taken as a limitation on the invention. Still further, in the drawings, the same reference numerals are employed for designating the same elements.

FIG. 1 shows an example of an inspection arrangement 10 for inspecting an elongate object 12 in accordance with at least one aspect of the present invention. It is to be appreciated that FIG. 1 is a schematic representation and is not intended to provide every possible specific detail of the example inspection arrangement 10 and is intended to simply convey at least one aspect of the invention.

The example inspection arrangement 10 includes a housing 16 within which inspection of a portion (e.g., a short segment) 12A of the elongate object 12 occurs as the elongate object is progressively moved through the housing. As such, each portion (e.g., 12A) of the elongate object 12 is sequential inspected. Moreover, a sequence of elongate objects (e.g., 12) can be moved through the housing 16 of the inspection arrangement 10 and thus each sequential elongate object (e.g., 12) can be sequentially inspected. This approach of sequential inspection provides for efficient inspection of such elongate objects (e.g., 12) via relative movement of the elongate objects through the housing 16 of the inspection arrangement 10.

The housing 16 encloses an interior space 20 within which the inspection occurs. The housing 16 has an entrance 22 into which the elongate object 12 is moved into the interior space 20. The housing 16 also has an exit 24 from which the elongate object 12 is moved out and away from the housing. The entrance 22 and the exit 24 are coaxially aligned along an axis 26. Thus, this alignment allows for the movement of the elongate object 12 into, through and out of interior space 20 of the housing 16 (i.e., movement relative to the interior space).

The example inspection arrangement 10 includes an ultrasonic detection device 28, which in turn includes a plurality of ultrasonic sensor arrays 30A-30D (two, 30A and 30C, are shown in FIG. 1) and an associated sensor array control and analysis portion 34. The ultrasonic sensor arrays 30A-30D (see FIG. 2) are disposed about the axis 26. Specifically, the plurality of sensor arrays 30A-30D is spaced to surround (e.g., encircle) a portion 20A of the interior space 20 and thus surrounds the portion 12A of the elongate object 12 located within the interior space. Within the shown example, four sensor arrays 30A-30D are provided and are respectively identified 30A-30D. It is to be appreciated that a different number (i.e., more or less than four) of the sensor arrays 30A-30D can be present. Herein, the sensor arrays may be generically/collectively referred to by just one reference number (e.g., 30D) with the understanding that the discussion is equally applicable to all/other sensor arrays (e.g., 30A-30D).

Each ultrasonic sensor array (e.g., 30D) contains a plurality of ultrasonic sensors 31 (only some shown and schematically shown). It is to be appreciated that specific details of the individual ultrasonic sensors 31 need not be specific limitations upon the present invention. Accordingly, details of the specific plurality of ultrasonic sensors 31 are omitted from the drawings. It is to be noted that each sensor 31 is constructed/configured to direct an ultrasonic sensory pluses 32, within the portion 20A of the interior space 20 of the housing 16 and thus toward or generally toward the portion 12A of the elongate object 12 located therein. Each ultrasonic sensor 31 also is constructed/configured to receive echo returns of the ultrasonic pluses from the portion 12A of the elongate object 12 located within the interior space 20. The return echoes convey information concerning the construction, structural integrity, flaws, and the like of the portion 12A of the elongate object 12 currently undergoing inspection within the interior 22 of the housing 16. It is to be appreciated that the control and processing of pulses and echoes need not be specific limitations upon the present invention. Single-sensor pulse/echo, multiple-sensor pulse/echo, specific sequencing, phasing, etc. are all contemplated as being usable within a configuration that includes the present invention.

Each sensor array (e.g., 30D) and the ultrasonic sensors 31 therein are operatively connected 36 (FIG. 1) to the sensor array control and analysis portion 34 such as by electrical connectors or the like. The sensor array control and analysis portion 34 controls operation of the sensor arrays 30A-30D and the ultrasonic sensors 31 therein. For example, the sensor array control and analysis portion 34 can cause/control sensor triggering (e.g., pulse firing) in a specific sequence pattern or the like). At the sensor arrays, the returned signals are converted, e.g., to electrical signals, as needed and conveyed to the sensor array control and analysis portion 34. The sensor array control and analysis portion 34 includes a processing arrangement that processes the signals in any desired manner to analyze information conveyed therein and thus discern the construction, structural integrity, flaws, and the like of the elongate object. The sensor array control and analysis portion 34 may include computers, software, hardware, processors, memory, and the like in order to accomplish this task. It is to be appreciated that the specifics of the sensor array control and analysis portion 34 need not necessarily be limitations of the present invention and are accordingly not described in detail herein.

It is to be appreciated that the ultrasonic sensory pluses and echoes are conveyed with greater efficiency via the presence and use of a coupling liquid fluid that couples the ultrasonic sensor arrays 30A-30D to the elongate object 12 being inspected. In one specific example, the coupling fluid is water although other suitable fluids could be used. The example inspection arrangement 10 in FIG. 1 includes a fluid delivery device 40 for delivering the coupling fluid into the interior space 20. The shown example of the fluid delivery device 40 includes a fluid source 42 and a plurality of inlet ports 46 directing the coupling fluid into the interior space 20.

Figure 3:
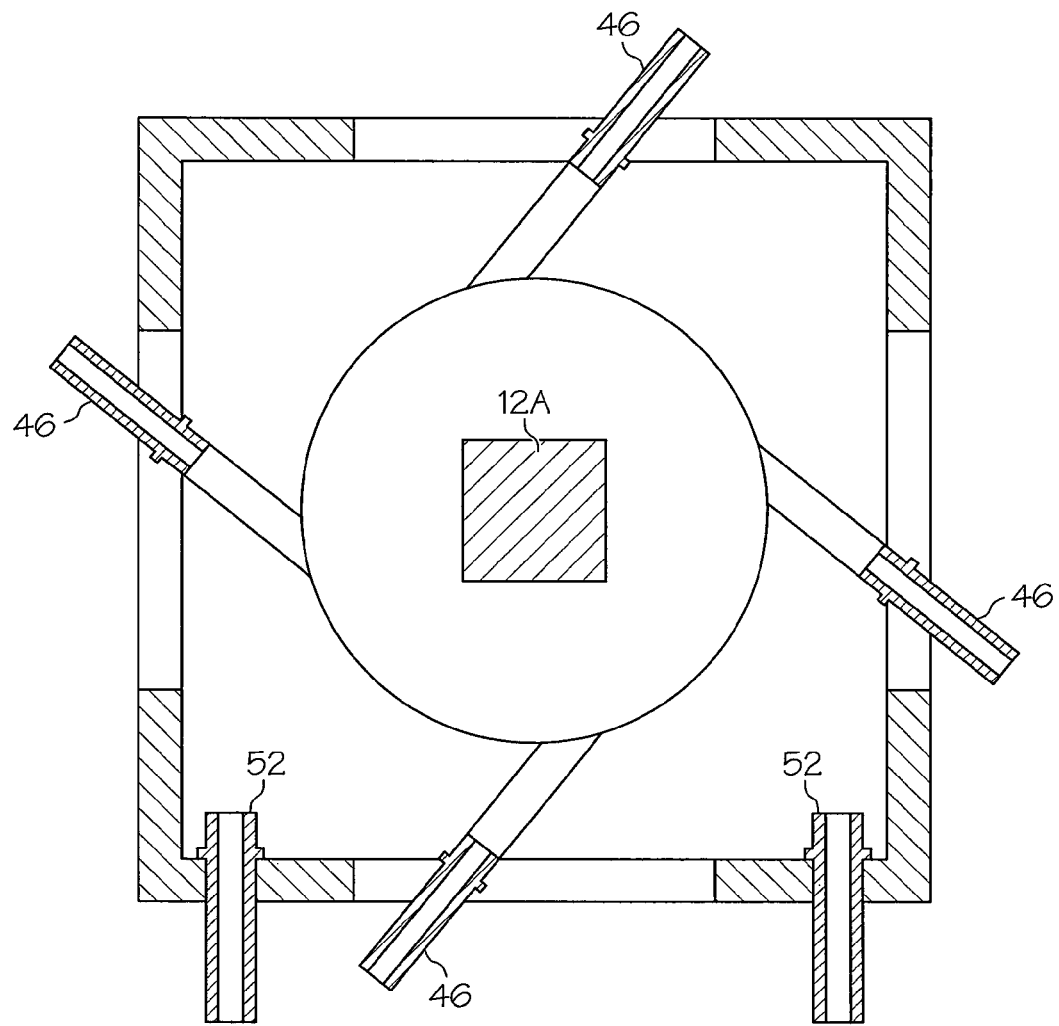
FIG. 3, is a section view taken along line 3-3 in FIG. 1, but with some background structure omitted, and shows fluid delivery into a housing interior for ultrasound pulse transmission.

Any suitable number of inlet ports 46 may be provided (see FIG. 3). The inlet ports 46 may be arranged to be spaced equidistantly around the perimeter of the interior space 20 and thus equidistantly spaced around the elongate object 12 present within the interior space. In addition, the inlet ports 46 may be oriented at angles or vectors to cause any desired fluid flow pattern, such as a moving or rotating fluid flow pattern. For example, within the shown example the inlet ports 36 of the fluid delivery device are angled such that the fluid is introduced into the interior space 20 with a generally tangential approach/flow within the interior space 20. Such introduction and flow helps to maintain constant presence of coupling fluid surrounding the elongate object 12 for transmission of the ultrasonic pluses/echoes there though. Still further, the inlet ports 36 may be arranged in groups or banks that are located at different locations (e.g., spaced axially). It is to be appreciated that such a type of inspecting arrangement can be referred to as a rotating water or "ROWA" inspecting arrangement. Of course, it is to be appreciated that the specifics of the fluid delivery device 40 and the delivery of fluid need not be specific limitations upon the present invention. As such, variations are contemplated.

The example inspection arrangement 10 includes a drain collection device 50 (FIG. 1) for draining/venting of the coupling fluid from the interior space 20 and collection of the coupling fluid. The coupling fluid can be recycled or disposed. Recycling may be via a recirculation pump of the drain collection device 50 for redistribution back into the interior space 20 via the inlet ports 46. Within the shown example, the drain collection device 50 includes drain vents 52 extending from the interior space 20, collection pans 54 into which the drain vents 52 exhaust the coupling fluid, and further drain vents 56 extending from the collection pans 54 for fluid to exit the collection pans. Of course, it is to be appreciated that the specifics of the drain collection device 50 and the draining/venting of the coupling fluid need not be specific limitations upon the present invention. As such, variations are contemplated.

The shown example of the inspection arrangement 10 also includes a pair of guidance members 60 for guiding the elongate object 12 through the interior space 20 of the housing 16 such that during movement of the elongate object, the object remains substantially centered upon the axis 26. Each guidance members 60 includes an aperture 62 centered on the axis 26 of the housing 16 that corresponds in close-fitting cross-sectional shape to the cross-sectional shape of the elongate object 12. The guidance members 60 permit the elongate object 12 to extend through the apertures 62 and move through the interior space 20 of the housing 16, but yet retain the object centered upon the axis 26.

In addition, the shown example of the inspection arrangement 10 includes a pair of sealing members 70. The sealing members 70 are located adjacent to the entrance 22 and the exit 24 and adjacent to the guidance members 60. The sealing members 70 axially seal the coupling fluid within the interior space 20 while the elongate object 12 is present and being inspected. The sealing members 70 are made of resilient material, such as an elastomer. Each sealing member 70 includes an aperture 72 centered on the axis 26 of the housing 16 that permits the elongate object 12 to extend through the apertures and thus move through the interior 20 of the housing. The aperture 72 corresponds in cross-sectional shape to the cross-sectional shape of the elongate object 12. The aperture 72 is sized and shaped such that the engagement between the sealing member 70 and the elongate object 12 is a close/bearing engagement (e.g., a tight interference fit) to prevent or minimize escape of the coupling fluid along the elongate object 12 past the sealing member.

It is to be appreciated that the guidance members 60 and the sealing members 70 can be removed and interchanged with different sealing members and guidance members that have apertures that are correspondingly sized/shaped in cross-section for different size/shape elongate objects (e.g., 12). Specifically, elongate objects (e.g., 12) having a different cross-sectional area (i.e., bigger or smaller) can be inspected within the inspection arrangement 10 by replacing the guidance members 60 and the sealing members 70 that have different sized/configured apertures. Thus, the elongate objects (e.g., 12) with different cross-sectional sizes/shapes, can be properly guided through the interior space 20 of the housing 16, with desired sealing of the coupling fluid within the interior housing, to accomplish the desired function of coupling the sensor arrays 30A-30D to the elongate object (e.g., 12) for transmission of the ultrasonic sensory pluses/echoes.

It is to be appreciated that objects that have an external circular cross-sectional area are often inspected. Another way of describing such an object is that it has an arcuate exterior surface. As such, the apertures 62 and 72 of the guidance members 60 and sealing members 70, respectively, will be provided to have interior circular cross-sectional shapes. However, within the shown example, the apertures 62 and 72 of the guidance members 60 and sealing members 70, respectively, have square cross-sectional shapes to accommodate the square cross-sectional shape of the example object 12 (e.g., has planar side surfaces). As mentioned, such square-aperture guidance members 60 and sealing members 70 can be provided via a replacement procedure.

Figure 2:
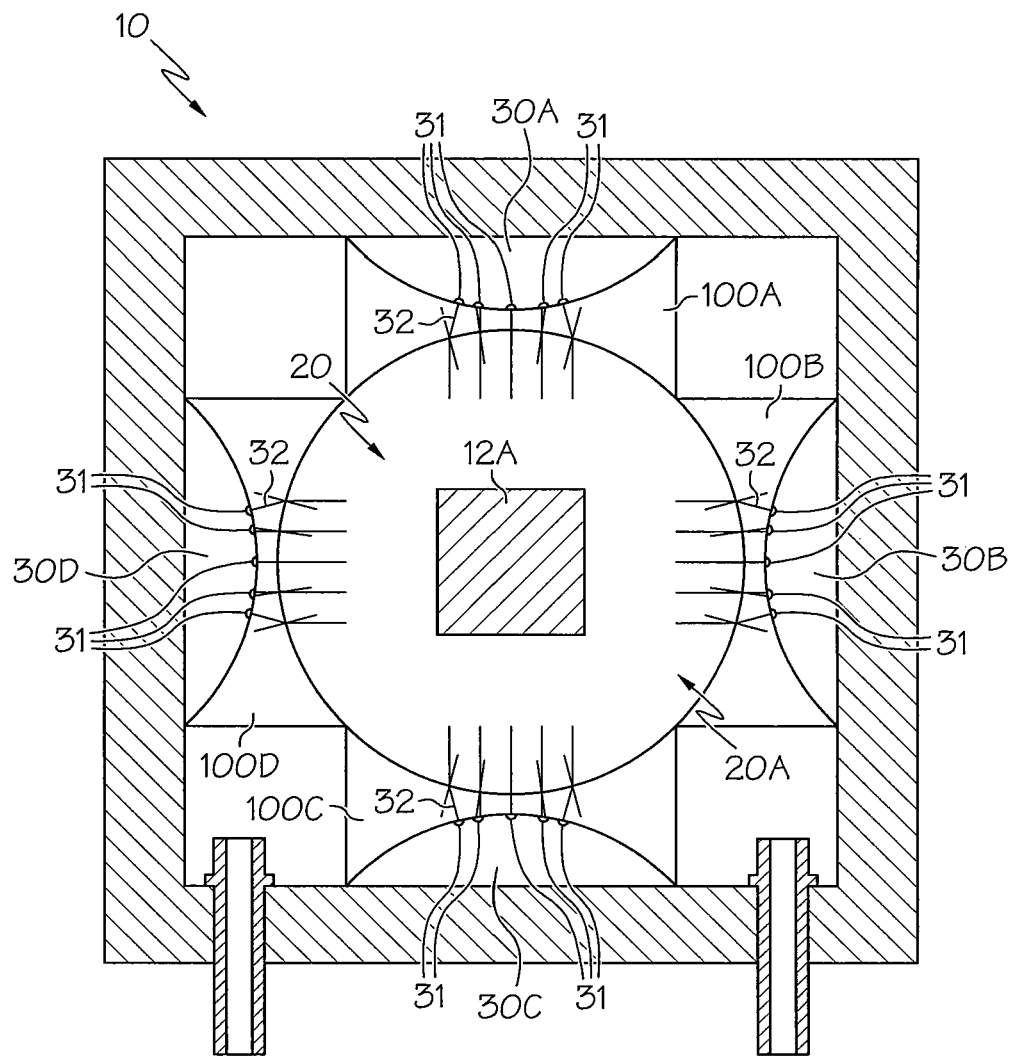
FIG. 2 is a section view taken along line 2-2 in FIG. 1, but with some background structure omitted, and shows a plurality of ultrasound sensor arrays and associated ultrasound redirecting elements in accordance with an aspect of the present invention.
Figure 4:
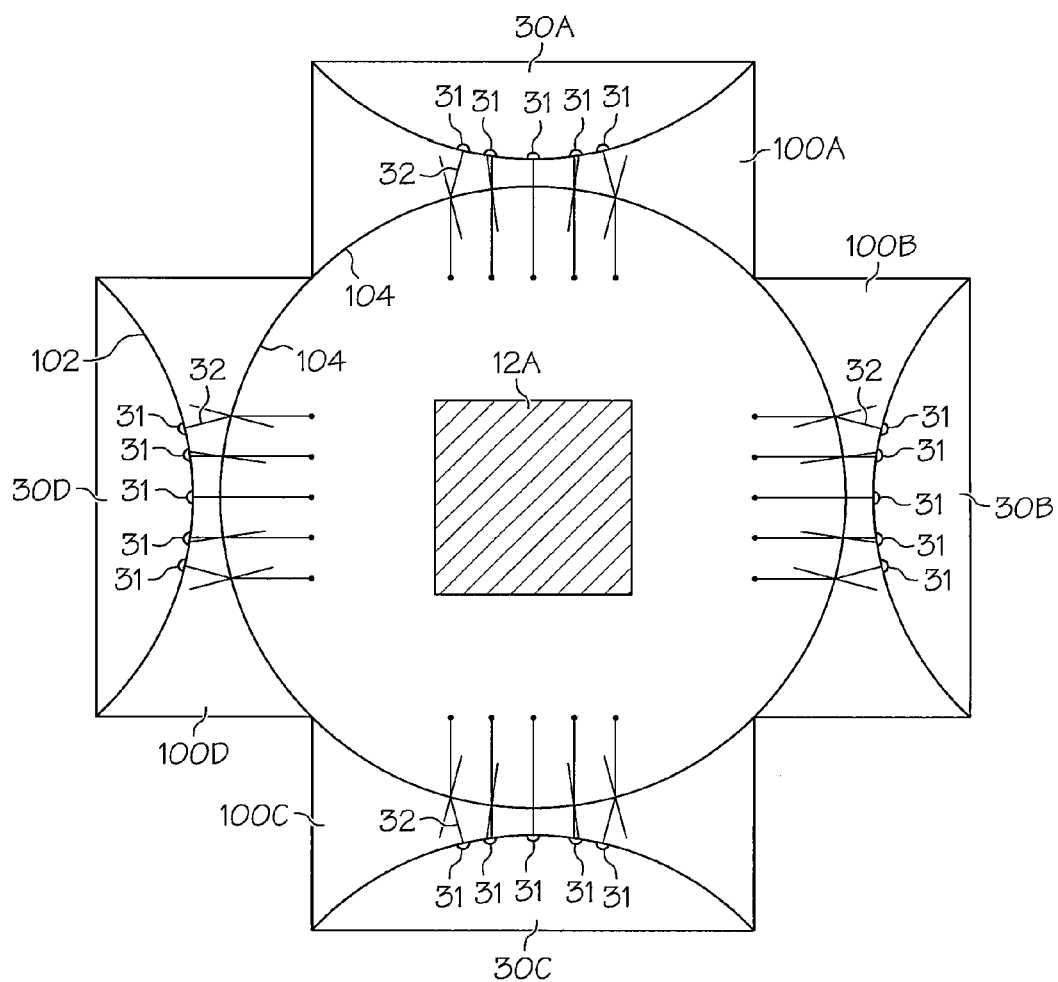
FIG. 4 is an enlarged view of a portion of the structures shown in FIG. 2 and specifically shows an example of redirection of ultrasonic sensory pluses for perpendicular interface with planar surfaces of the object in accordance with an aspect of the present invention.

It is to be appreciated that not only does the inspection arrangement 10 have the ability to be reconfigured, via replacement of the guidance members 60 and the sealing members 70, to readily accept elongate objects having non-circular cross-sectional areas, in accordance with the present invention, the inspection arrangement 10 provides for improved sensing ability of the objects having non-circular cross-sectional areas. Specifically, the plurality of ultrasonic sensor arrays 30A-30D, alone, within the shown example inspection arrangement 10 are pre-configured to provide optimal sensory inspection of elongate objects having a circular cross-sectional area (e.g., a circular cross-sectional solid or a circular cross-sectional hollow pipe). In the shown example, the configuration of each ultrasonic sensor array is such that the each sensor array is convexly curved face and has a center apex as its most distal point. However, in accordance with an aspect of the present invention, a plurality of redirecting elements 100A-100D can be placed within the interior 20 of the housing 16, and associated with the plurality of ultrasonic sensor arrays 30A-30D, to provide improved inspection of non-circular cross-sectional area elongate objects (e.g., the square cross-sectional area object 12). The aspect that the example object 12 has a non-circular cross section is best seen in FIG. 2-4. With the shown example, the cross-sectional area of the object 12 is a square.

The redirecting elements 100A-100D (see FIGS. 2 and 4) are associated with the ultrasonic sensor arrays 30A-30D are thus disposed about the axis 26. It is to be appreciated that a different number (i.e., more or less than four) of the redirecting elements 100A-100D can be present. Herein, the redirecting elements may be generically/collectively referred to by just one reference number (e.g., 100D) with the understanding that the discussion is equally applicable to all/other redirecting elements (e.g., 100A-100D).

The redirecting elements 100A-100D are located adjacent to a respective one of the ultrasonic sensor arrays 30A-30D and interposed between the sensor arrays 30A-30D and the object 12. The redirecting elements 100A-100D are spaced to surround (e.g., encircle) the portion 20A (see FIG. 1) of the interior space 20 and thus surrounds the portion 12A of the elongate object 12 located within the interior space. Within the shown example, there are four redirecting elements 100A-100D to correspond to the four sensor arrays 30A-30D (see FIGS. 2 and 4). The four redirecting elements are individually, respectively identified with reference numbers 100A-100D.

Figure 5:
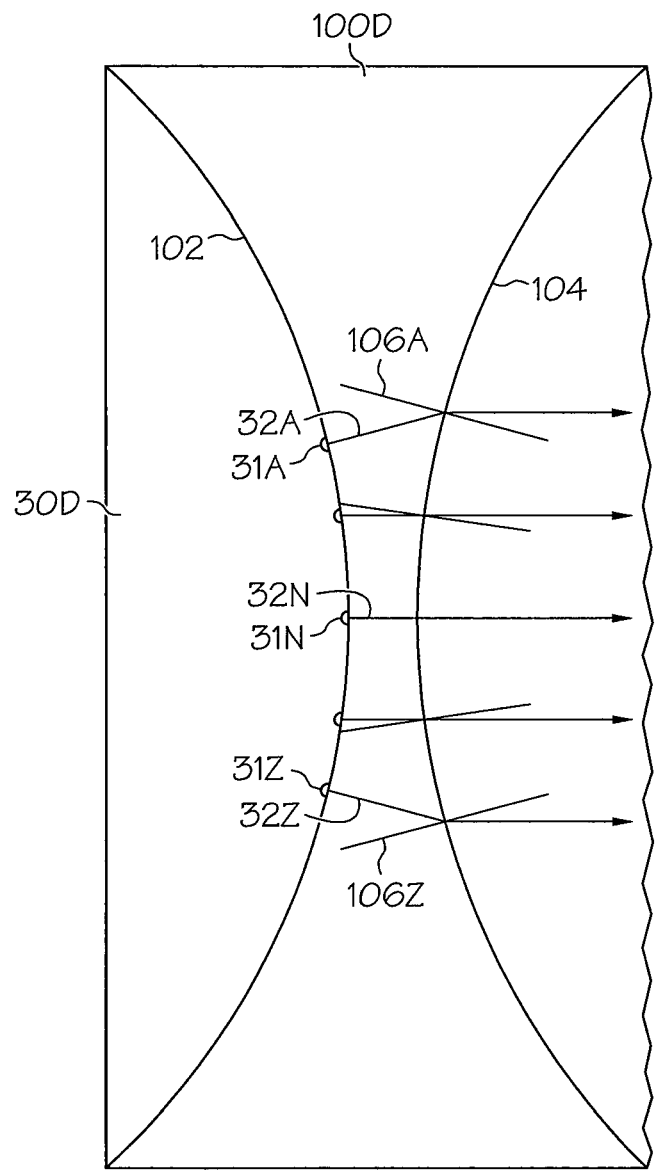
FIG. 5 is a further enlargement of a portion of the structures shown in FIG. 4 and shows a single ultrasonic sensor array and a single associated redirecting element in accordance with an aspect of the present invention.

Turning attention to FIGS. 4 and 5, schematic representations of the plurality of ultrasonic sensor arrays 30A-30D and the associated redirecting elements 100A-100D are shown. As will be recalled, each ultrasonic sensor array (e.g., 30D) is configured to have a plurality of ultrasonic sensors. Each ultrasonic sensor is positioned/configured such that its respective ultrasonic sensory pulse 32 is directed along a specific direction. For the shown example ultrasonic sensor arrays 30A-30D, the directions of the plurality of ultrasonic sensory pulses 32 are not identical in that the pulses 32 move along directions that are divergent or spread as the pulses proceed away from the respective ultrasonic sensor array 30A-30D. Such a configuration is very effective for inspection of circular cross-sectional elongate objects. However, such an ultrasonic sensor array configuration, alone, has lesser effectiveness concerning inspection of non-circular cross-sectional area elongate objects (e.g., the square cross-sectional object 12). In accordance with an aspect of the present invention, each redirecting element (e.g., 100D) redirects at least some of the ultrasonic sensory pulses 32 proceeding from the respective sensor array 30A-30D so that inspection of objects that have non-circular cross-sectional areas (e.g., square in the present example) may be better accomplished.

The ultrasonic pulses 32 proceed or travel through the redirecting elements 100A-100D, and the redirecting elements 100A-100D provide a redirecting function. The redirecting elements 100A-100D may provide the redirecting function based upon surface contour (e.g., concave face) and/or material property (e.g., refraction). In some general examples, the material of the redirecting elements 100A-100D may be plastic or glass. In one specific example, the material of the redirecting elements 100A-100D is commercially available LUCITE®. For the example of the material being LUCITE, the ultrasonic sensor pulses of one example travel at a speed of 2,740 meters per second through the LUCITE, which is in comparison to a travel speed of 1,480 meters per second of the same pulses traveling through water as the coupling fluid. Within the shown example, each redirecting element (e.g., 100D) is a by-concave element in that has both a leading face 102 and a trailing face 104 are concave. The leading face 102 is a first concave face and the trailing face 104 is a second concave face. The trailing (second) face 104 faces or presents toward a respective planar side surface of the square cross-sectional object 12.

Turning to the redirection of at least some of the ultrasonic sensory pulses, attention is directed to FIG. 4 in which one pulse is generically labeled 32A to represent a pulse proceeding from a sensor 31A located at first side of a center apex of the sensor array 30D, another pulse is generically labeled 32N to represent a pulse proceeding from a sensor 31N located at an apex of the sensor array 30A-30D, and yet another pulse is generically labeled 32Z to represent a pulse proceeding from a sensor 31Z located at a second side of the apex of the sensor. It is to be appreciated that alphabetic suffixes are not intended to connote the number of pulse-producing sensors that are present within an array. In addition, it is to be appreciated that other, non-illustrated pulses may be present as then proceed from other, different sensors of the sensor array.

Note that in FIG. 4, the ultrasonic sensory pulse 32N proceeding from the apex of the ultrasonic sensory array proceeds generally directly through the redirecting element (e.g., 100D) with little or no significant change of direction of the ultrasonic sensory pulse. However, for ultrasonic sensory pulses (e.g., 32A or 32Z) proceeding from respective ultrasonic sensors spaced away from this apex of the ultrasonic sensor array, the ultrasonic sensory pulses have changes or re-directions to their path or course via the redirecting element (e.g., 100D). It is to be appreciated that for the present example, pulses that have a greater offset from the apex will have greater amounts of change or re-direction of their path or course. To help visualize such re-direction normal (i.e., perpendicular) lines 106A-106Z are indicated on the trailing face 104.

Turning to a focus upon the now redirected ultrasonic sensor pulses 32 of the presented example, as the plurality of ultrasonic sensor pulses proceed from the redirecting element (e.g., 100D) and into the coupling fluid (e.g., water) it should be appreciated that the ultrasonic sensory pulses 32 now all have generally parallel courses of direction. As a descriptor it could be considered to be analogous to collimation of light. Thus, the ultrasonic sensory pulses 32 can be considered to be upon parallel courses of direction. With such parallel course, the ultrasonic sensory pulses 32 all generally impinge upon a surface of the non-circular cross section elongate object in a perpendicular or normal manner to the planar side surface of the square cross-sectional object 12. The return echoes thus have an improved ability to proceed back to the sensor array (e.g., 30D) to convey sensory information.

Of course, echoes that return back from the object also proceed through the redirecting element (e.g., 100D). During such return travel, the echoes may also redirected. The redirection can be considered to be somewhat of a reversal of that which occurred to the pulses that initially traveled through the redirecting element.

Via another aspect, the present invention provides an associated method of providing the inspection arrangement 10 for inspecting the elongate object 12. The method includes providing the housing 16 with the interior space 20 within which inspection is to occur. The housing 16 has the entrance 22 and the exit 24 that are aligned on the axis 26 for respective movement of the object 12 relative to the interior space 20. The method includes providing the plurality of ultrasonic sensor arrays 30A-30D disposed about the axis 26 to direct ultrasonic sensory pluses 32 within the housing 16. Each sensor array (e.g., 30D) has the plurality of ultrasonic sensors 31A-31Z with each ultrasonic sensor being positioned to direct the respective ultrasonic sensory pulse 32 in a respective direction within the interior space 20. The method includes providing the fluid delivery device 40 for delivering the coupling fluid into the interior space. The coupling fluid engages the elongate object 12 and transmits the ultrasonic sensory pluses 32 to the elongate object. The method includes providing the plurality of redirecting elements 100A-100D associated with the plurality of ultrasonic sensor arrays 30A-30D. Each redirecting element (e.g., 100D) is positioned such that ultrasonic sensory pluses 32 from the respective ultrasonic sensor array (e.g., 30D) proceed through the respective redirecting element. Each redirecting element (e.g., 100D)

redirecting at least some of the ultrasonic sensory pulses 32 to proceed along a different direction.

Several sub-aspects of such a method are also provided for example, the step of providing the plurality of redirecting elements includes providing each redirecting element in a configuration to redirect the ultrasonic pulses proceeding there through to emerge from the redirecting element and proceed along parallel directions. As another example, the step of providing a plurality of ultrasonic sensor arrays includes providing each sensor array such that the plurality of ultrasonic sensors are positioned to direct the respective ultrasonic sensory pulses in respective directions for inspecting an elongate object having an arcuate exterior surface, and the step of providing the plurality of redirecting elements includes providing each redirecting element to be configured to redirect the ultrasonic pulses proceeding there through for inspecting an elongate object having a planer surface. As another example, the step of providing a plurality of ultrasonic sensor arrays includes providing each sensor array to have a convex face, and the step of providing the plurality of redirecting elements includes providing each redirecting element to be configured to have a concave face mating to the convex face of a respective sensor array. As yet another example, the step of providing the plurality of redirecting elements includes providing each redirecting element to be configured such that the concave face is a first concave, and each redirecting element has a second concave face.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. An inspection arrangement for inspecting an elongate object having a plurality of planar side surfaces, the arrangement including:
    a housing providing an interior space within which inspection is to occur, the housing having an entrance and an exit that are aligned on an axis for respective movement of the object relative to the interior space;
    a plurality of ultrasonic sensor arrays disposed about the axis to direct ultrasonic sensory pluses within the housing, each sensor array having a plurality of ultrasonic sensors with each ultrasonic sensor being positioned to direct a respective ultrasonic sensory pulse in a respective direction within the interior space;
    a fluid delivery device for delivering a coupling fluid into the interior space, the coupling fluid engages the elongate object and transmits the ultrasonic sensory pluses to the elongate object; and
    a plurality of redirecting elements associated with the plurality of ultrasonic sensor arrays, the number of redirecting elements being equal to the number of planar side surfaces of the elongate object, each redirecting element positioned such that ultrasonic sensory pulses from the respective ultrasonic sensor array proceed through the respective redirecting element, each redirecting element for redirecting at least some of the ultrasonic sensory pulses to proceed along a different direction and including at least one surface redirecting at least some of the ultrasonic pulses such that the ultrasonic pulses emerge from the redirecting element and proceed along parallel directions toward a respective planar side surfaces of the elongate object.

2. An inspection arrangement as set forth within claim 1, wherein for each sensor array the plurality of ultrasonic sensors are positioned to direct the respective ultrasonic sensory pulses in respective directions for inspecting an elongate object having an arcuate exterior surface, and each redirecting element being configured to redirect the ultrasonic pulses proceeding there through for inspecting an elongate object having a planer surface.

3. An inspection arrangement as set forth within claim 1, wherein each ultrasonic sensor array has a convex face, and each redirecting element has a concave face mating to the convex face of a respective sensor array.

4. An inspection arrangement as set forth within claim 3, wherein for each redirecting element the concave face is a first concave, each redirecting element has a second concave face.

5. An inspection arrangement as set forth within claim 1, wherein elongate object has a square cross-section.

6. An inspection arrangement as set forth within claim 1, wherein the redirecting elements are configured to direct the ultrasonic sensory pluses to generally impinge upon a respective planar side surface of the object in a perpendicular manner to the planar surface.

7. A method of providing an inspection arrangement for inspecting an elongate object having a plurality of planar side surfaces, the method including:
    providing a housing with an interior space within which inspection is to occur, the housing having an entrance and an exit that are aligned on an axis for respective movement of the object relative to the interior space;
    providing a plurality of ultrasonic sensor arrays disposed about the axis to direct ultrasonic sensory pluses within the housing, each sensor array having a plurality of ultrasonic sensors with each ultrasonic sensor being positioned to direct a respective ultrasonic sensory pulse in a respective direction within the interior space;
    providing a fluid delivery device for delivering a coupling fluid into the interior space, the coupling fluid engages the elongate object and transmits the ultrasonic sensory pluses to the elongate object; and
    providing a plurality of redirecting elements associated with the plurality of ultrasonic sensor arrays, the number of redirecting elements being equal to the number of planar side surfaces of the elongate object, each redirecting element positioned such that ultrasonic sensory pluses from the respective ultrasonic sensor array proceed through the respective redirecting element, each redirecting element for redirecting at least some of the ultrasonic sensory pulses to proceed along a different direction and including at least one surface redirecting at least some of the ultrasonic pulses such that the ultrasonic pulses emerge from the redirecting element and proceed along parallel directions toward a respective planar side surfaces of the elongate object.

8. A method as set forth within claim 7, wherein the step of providing a plurality of ultrasonic sensor arrays includes providing each sensor array such that the plurality of ultrasonic sensors are positioned to direct the respective ultrasonic sensory pulses in respective directions for inspecting an elongate object having an arcuate exterior surface, and the step of providing the plurality of redirecting elements includes providing each redirecting element to be configured to redirect the ultrasonic pulses proceeding there through for inspecting an elongate object having a planer surface.

9. A method as set forth within claim 7, wherein the step of providing a plurality of ultrasonic sensor arrays includes providing each sensor array to have a convex face, and the step of providing the plurality of redirecting elements includes providing each redirecting element to be configured to have a concave face mating to the convex face of a respective sensor array.

10. A method as set forth within claim 9, wherein the step of providing the plurality of redirecting elements includes providing each redirecting element to be configured such that the concave face is a first concave, each redirecting element has a second concave face.

11. A method as set forth within claim 7, wherein elongate object has a non-circular cross-section.

12. A method as set forth within claim 7, wherein elongate object has a square cross-section.

13. A method as set forth within claim 7, wherein the step of providing the plurality of redirecting elements includes providing each redirecting element to be configured to direct the ultrasonic sensory pluses to generally impinge upon a respective planar side surface of the object in a perpendicular manner to the planar surface.

\* \* \* \* \*